United States Patent
Garbey et al.

(10) Patent No.: US 10,470,687 B2
(45) Date of Patent: Nov. 12, 2019

(54) SURGICAL PROCEDURE MANAGEMENT SYSTEMS AND METHODS

(71) Applicants: UNIVERSITY OF HOUSTON, Houston, TX (US); THE METHODIST HOSPITAL, Houston, TX (US)

(72) Inventors: Marc Garbey, Houston, TX (US); Barbara Lee Bass, Houston, TX (US); Brian James Dunkin, Houston, TX (US); Vadim Sherman, Houston, TX (US); Giulia Toti, Houston, TX (US)

(73) Assignees: University of Houston, Houston, TX (US); The Methodist Hospital, Houston, TX (US)

( * ) Notice: Subject to any disclaimer, the term of this patent is extended or adjusted under 35 U.S.C. 154(b) by 148 days.

(21) Appl. No.: 14/099,430

(22) Filed: Dec. 6, 2013

(65) Prior Publication Data
US 2014/0171787 A1   Jun. 19, 2014

Related U.S. Application Data

(60) Provisional application No. 61/734,506, filed on Dec. 7, 2012.

(51) Int. Cl.
| | |
|---|---|
| A61B 5/05 | (2006.01) |
| A61B 5/06 | (2006.01) |
| A61B 90/90 | (2016.01) |
| A61B 90/94 | (2016.01) |
| A61B 90/98 | (2016.01) |
| A61B 5/00 | (2006.01) |

(Continued)

(52) U.S. Cl.
CPC .............. *A61B 5/061* (2013.01); *A61B 5/064* (2013.01); *A61B 90/90* (2016.02); *A61B 90/94* (2016.02); *A61B 90/98* (2016.02); *A61B 5/6847* (2013.01); *A61B 2034/2051* (2016.02); *A61B 2034/2065* (2016.02); *A61B 2090/3983* (2016.02)

(58) Field of Classification Search
None
See application file for complete search history.

(56) References Cited

U.S. PATENT DOCUMENTS

| | | | |
|---|---|---|---|
| 5,836,869 A | 11/1998 | Kudo et al. | |
| 7,876,942 B2 * | 1/2011 | Gilboa | A61B 6/12 382/128 |

(Continued)

FOREIGN PATENT DOCUMENTS

| | | |
|---|---|---|
| WO | WO 2011-020505 A1 | 8/2009 |
| WO | WO 2011-133873 A1 | 10/2011 |

OTHER PUBLICATIONS

Kranzfelder M., et al. "Feasibility of opto-electronic surgical instrument identification." Minimally Invasive Therapy & Allied Technologies, Nov. 18, 2009, No. 5, pp. 253-258.*

(Continued)

*Primary Examiner* — Joel F Brutus
(74) *Attorney, Agent, or Firm* — ParkerHighlander PLLC

(57) ABSTRACT

Systems and methods for tracking a surgical tool. Exemplary embodiments can comprise a surgical port, a tracking element configured for coupling to a surgical tool, and a camera mounted to a proximal end of the surgical port and configured to capture image data associated with the tracking element.

12 Claims, 8 Drawing Sheets

(51) Int. Cl.
A61B 90/00 (2016.01)
A61B 34/20 (2016.01)

(56) References Cited

U.S. PATENT DOCUMENTS

| | | | | |
|---|---|---|---|---|
| 2004/0028258 | A1* | 2/2004 | Naimark | G06K 9/4609 382/103 |
| 2008/0262654 | A1* | 10/2008 | Omori | A61B 19/22 700/245 |
| 2009/0312629 | A1* | 12/2009 | Razzaque | A61B 5/06 600/426 |
| 2009/0327715 | A1* | 12/2009 | Smith | A61B 1/018 713/168 |
| 2010/0056900 | A1 | 3/2010 | Whitcomb et al. | |
| 2011/0119224 | A1* | 5/2011 | Mangione-Smith | A61B 6/12 706/52 |
| 2012/0078236 | A1* | 3/2012 | Schoepp | A61B 5/061 606/1 |
| 2014/0107471 | A1* | 4/2014 | Haider | A61B 17/1703 600/424 |

OTHER PUBLICATIONS

Agarwal S, et al., "A Pervasive Computing System for the Operating Room of the Future." *Mobile Networks and Applications*, 2007; 12:215-28.

Blum T, et al., "Modeling and online recognition of surgical phases using Hidden Markov Models." *Med Image Comput Assist Interv.* 2008;11:627-3.

Doryab A, et al., "Designing activity-aware recommender systems for operating rooms." *Proceedings of the 2011 Workshop on Context-awareness in Retrieval and Recommendation.* New York, NY, USA; 2011;43-6.

Doryab A, et al., "Activity-aware recommendation for collaborative work in operating rooms." *Proceedings of the 2012 ACM international conference on Intelligent User Interfaces.* New York, NY, USA; 2012;301-4.

Kranzfelder, M. et al. "New technologies for information retrieval to achieve situational awareness and higher patient safety in the surgical operating room: the MRI institutional approach and review of the literature." *Surg. Endosc* (201) 25:696-705.

Liu CC, et al., "RFID-initiated workflow control to facilitate patient safety and utilization efficiency in operation theater." *Comput Methods Programs Biomed.* 2011; 104(3):435-42.

Marjamaa R, et al., "Operating room management: why, how and by whom?" *Acta Anaesthesiologica Scandinavica.* 2008;52:596-600.

Neumuth D, et al., "Modeling surgical processes: a four-level translational approach." *Artif Intell Med. Netherlands.* 2011;51(3):147-61.

Neumuth T, et al., "Analysis of surgical intervention populations using generic surgical process models." *Int J Comput Assist Radiol Surg.* 2011;6:59-71.

Neumuth T, et al., "Validation of knowledge acquisition for surgical process models." *J Am Med Inform Assoc.* 2009;16(1):72-80.

Neumuth T, et al., "Acquisition of Process Descriptions from Surgical Interventions." *Lecture notes in computer science.* 2006;4080:602-11.

Padoy N, et al., "Statistical modeling and recognition of surgical workflow." *Medical Image Analysis.* 2012;16:632-41.

PCT International Search Report and Written Opinion issued in International Application No. PCT/US2013/073592, dated Mar. 27, 2014.

Extended European Search Report and Opinion issued in European Patent Application No. 13860374, dated Nov. 16, 2016.

* cited by examiner though the camera is movable on the surgical port. In certain embodiments, the camera is directed towards the tracking element. In specific embodiments, the camera is directed away from the body of the patient. In particular embodiments, the camera includes a light element for illuminating the tracking element.

SURGICAL PROCEDURE MANAGEMENT SYSTEMS AND METHODS

CROSS-REFERENCE TO RELATED APPLICATION

This application claims priority to U.S. Provisional Patent Application Ser. No. 61/734,506, filed Dec. 7, 2012, the entire contents of which are incorporated herein by reference.

TECHNICAL FIELD

Exemplary embodiments of the present disclosure relate to a surgical tool tracking system utilizing a camera to track various surgical tools and provide procedure management information to the user.

BACKGROUND

Laparoscopic surgery is a common and popular alternative to open surgery due to the considerable reduction of recovery time, pain and complications. However, many obstacles make the surgeon's work difficult and inefficient, including limited access to the operating field, indirect vision, and operating theaters originally built for open surgery. There has been an interest in the field to develop systems to aid in "operating room awareness." Operating room awareness refers to creating an operating room that can collect data related to the operation in progress and use the data to assist the surgeon and medical staff. There is also interest using the collected data to assist in surgeon/staff training and evaluation.

One component of operating room awareness is tool identification, location and navigation. Historically, surgical tools have been identified using visual inspection by the surgeon and/or medical staff. Some automated systems exist; however, the accuracy of these systems can be compromised by the presence of metals and fluids in the operating space and the reliance on a constantly-changing point of reference for the tracking device.

Therefore, a need in the art exists for a minimally intrusive, yet robust, system to analyze data generated during a medical procedure and provide real-time context awareness to the surgery team as well as post-procedure evaluation tools.

SUMMARY OF THE INVENTION

Presented are systems and methods for surgical tool tracking and an information management system for managing medical procedure information.

Certain embodiments include a surgical tool tracking system comprising a surgical port comprising a proximal end configured to be located outside a body of a patient and a distal end configured to be located within an internal portion of the body of the patient, and a channel extending between the proximal end and the distal end. Particular embodiments include a tracking element configured for coupling to a surgical tool, and a camera mounted to the proximal end of the surgical port and configured to capture image data associated with the tracking element.

In specific embodiments, the surgical port is a trocar, the trocar comprising a base at the proximal end and a cannula at the distal end, wherein the camera is mounted to the base. In particular embodiments, the camera is in a fixed position with respect to the surgical port, while in other embodiments the camera is movable on the surgical port. In certain embodiments, the camera is directed towards the tracking element. In specific embodiments, the camera is directed away from the body of the patient. In particular embodiments, the camera includes a light element for illuminating the tracking element.

Certain embodiments comprise a computer system, wherein the camera is in communication with the computer system to transmit the image data to the computer system. In specific embodiments, the tracking element includes at least one of a color, a shape, a pattern, bar code, and a character. Particular embodiments comprise a surgical tool, where the surgical tool is sized and configured to access the internal portion of the body of the patient through the channel of the surgical port, and the tracking element is coupled to the surgical tool. In specific embodiments, the tracking element corresponds to at least one of an identity of the surgical tool, an orientation of the surgical tool, and a position of the surgical tool. In certain embodiments, the tracking element is positioned a location proximate a handle associated with the surgical tool. In particular embodiments, the camera is further configured to capture image data associated with a surgeon.

Exemplary embodiments also include a method of tracking a surgical tool comprising: providing a surgical tool to a surgical port, the surgical tool including a tracking element and the surgical port including a camera mounted thereto; capturing image data at the camera; providing the image data to a processor; and determining, at the processor, tracking information associated with the surgical tool. In certain embodiments, providing the surgical tool to the surgical port further includes, inserting a portion of the surgical tool into a channel extending between a proximal end and a distal end of the surgical port. In particular embodiments, the tracking information includes at least one of an identity of the surgical tool, an orientation of the surgical tool, a position of the surgical tool, and an identity of a surgeon. In specific embodiments, the image data is associated with at least one of the tracking element and a surgeon.

Exemplary embodiments include a method for managing medical procedure information comprising: receiving image data from a camera associated with the a surgical port, the image data representative of a tracking element associated with a surgical tool; determining an identity and a location of the surgical tool based on the image data; determining a surgical step of a medical procedure using the image data; and determining procedure management information by comparing the image data associated with the surgical step with the medical procedure; where the image data is not associated with a particular finite set of known tools.

In particular embodiments, the image data is further includes image data associated with a surgeon. In certain embodiments, determining the identity of the surgical tool comprises comparing the image data associated with the tracking element with stored data to identify a corresponding stored surgical tool identity. In specific embodiments, determining the location of the surgical tool comprises comparing the image data associated with the tracking element and location information associated with the surgical port.

In particular embodiments, determining the location of the surgical tool comprises analyzing the image data associated with the tracking element to determine at least one of an orientation of the surgical tool with respect to the surgical port and a position of the surgical tool with respect to the surgical port. In certain embodiments, determining the location of the surgical tool includes determining a location of the surgical tool in a treatment room associated with the surgical procedure. Specific embodiments comprise calculating a time to completion of a surgical procedure associated with the surgical step.

Particular embodiments also comprise determining a time of use associated with at least one of the surgical tool and the surgical port. In certain embodiments, the management information includes an efficiency of the surgical procedure. In particular embodiments, the management information includes a skill level associated with a surgeon performing the surgical procedure. In particular embodiments, the image data includes image data from a plurality of surgical ports, the image data representative of a plurality of tracking elements associated with a corresponding plurality of surgical tools.

Certain embodiments further comprise: receiving image data from a second camera associated with the a second surgical port, the image data representative of a second tracking element associated with a second surgical tool; determining an identity and a location of the second surgical tool based on the image data; and determining a next surgical step using the image data. In particular embodiments, determining the procedure management information further includes: comparing the image data associated with the next surgical step with the medical procedure; and comparing the next surgical step with the first surgical step.

An aspect of the present disclosure is directed to a surgical tool tracking system. The surgical tool tracking system includes a surgical port, and a tracking element associated with a surgical tool and a camera. The surgical port may have a proximal end configured to be located outside the body of a patient and a distal end configured to be located within an internal portion of the body of the patient. The surgical port may also have a channel extending between the proximal end and the distal end. The surgical tool may be sized and configured to access the internal portion of the body of the patient through the channel of the surgical port. The tracking element may be removably coupled to the surgical tool and a camera mounted to the proximal end of the surgical port may be configured to capture image data associated with the tracking element.

Another aspect of the present disclosure is directed to a method of tracking a surgical tool. The method may include providing a surgical tool to a surgical port where the surgical tool may include a tracking element and the surgical port may include a camera mounted thereto. The method may further include capturing image data at the camera. The method may further include providing the image data to a processor and determining, at the processor, tracking information associated with the surgical tool.

A further aspect of the present disclosure is directed to an information management system for managing medical procedure information. The system may receive image data from a camera associated with a surgical port, the image data representative of a tracking element associated with a surgical tool. The image data is not associated with a particular finite set of known tools. The system may further determine an identity and a location of the surgical tool based on the image data. The system may also determine a surgical step of a medical procedure using the image data and determine procedure management information by comparing the image data associated with the surgical step with the medical procedure.

The details of one or more embodiments of the invention are set forth in the accompanying drawings and the description below.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

Exemplary embodiments of the present disclosure are provided in the following drawings. The drawings are merely examples to illustrate the structure of exemplary devices and certain features that may be used singularly or in combination with other features. The invention should not be limited to the examples shown.

DETAILED DESCRIPTION

Figure 1:
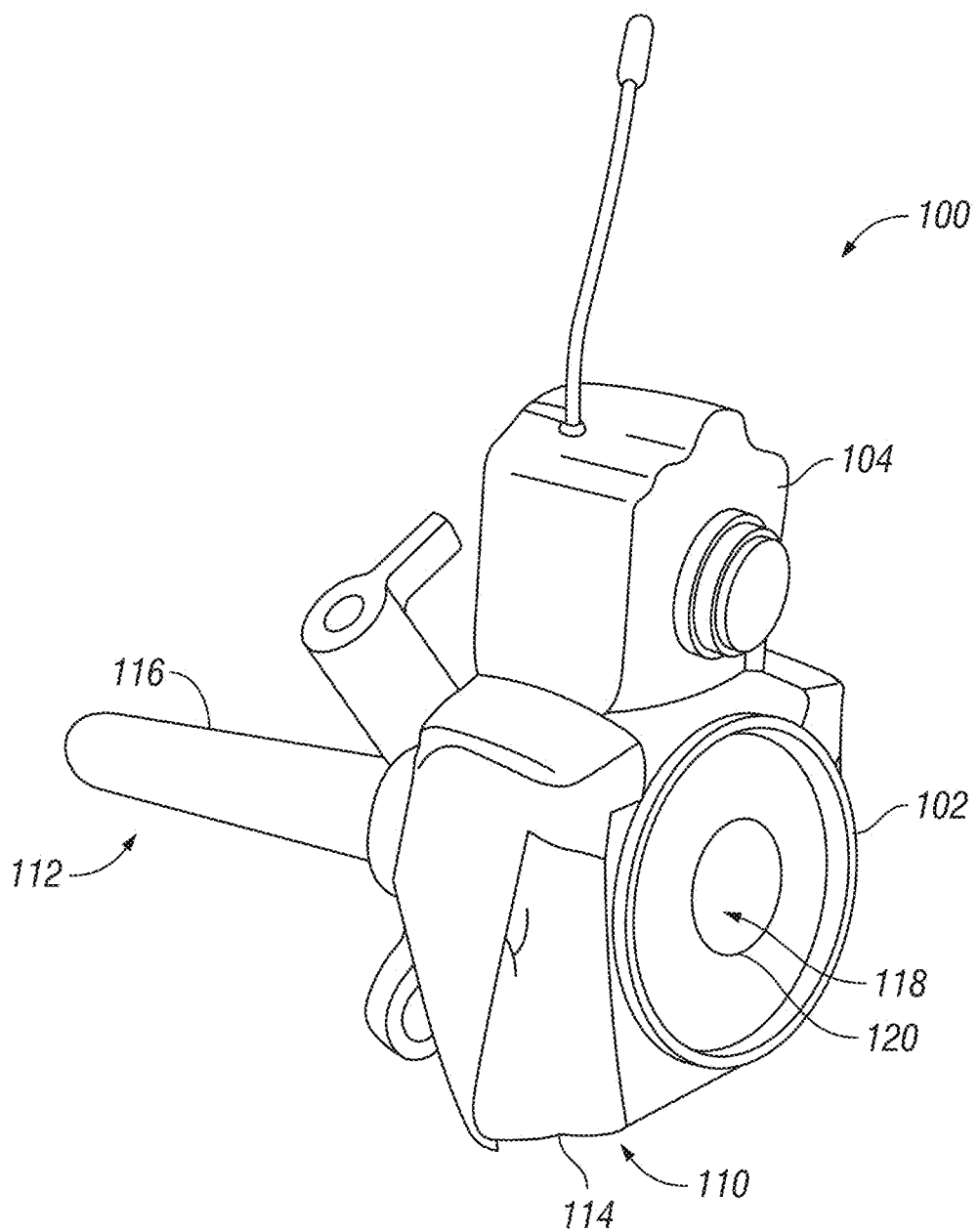
FIG. 1 is a perspective view of an example surgical tracking tool.

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "approximately" or "substantially" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Figure 2:
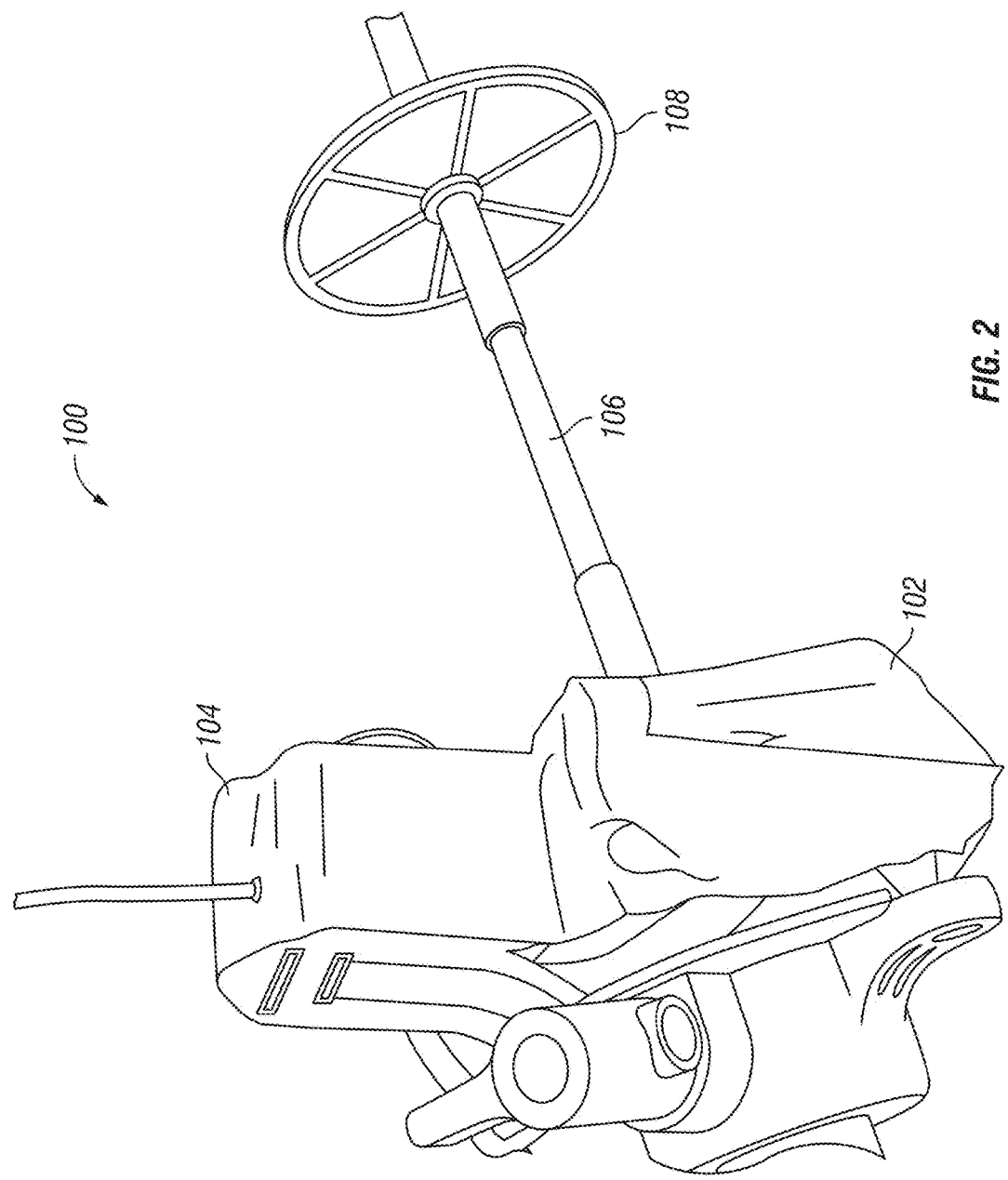
FIG. 2 is a perspective view of an example surgical tracking tool.

Certain examples of the invention will now be described with reference to the drawings. In general, such examples relate to the use of a surgical tool tracking system that uses a camera to track surgical tools and provide procedure management information to the user. FIGS. 1 and 2 provide perspective views of one exemplary embodiment of a surgical tool tracking system 100. In the embodiment shown, surgical tool tracking system 100 can include a surgical port 102, a camera 104 coupled to the surgical port 102, and a corresponding tracking element 108 associated with a surgical tool 106.

In exemplary embodiments, surgical port 102 can be placed into incision in a patient's body and provide an access point through which surgical instruments may be introduced into an internal surgical site. In certain embodiments, surgical port 102 can include a needle, a cannula, a trocar, or any other style of surgical port known in the art. Surgical port 102 can be composed of a biocompatible material. It is contemplated that the surgical port 102 can be constructed from a disposable material thereby reducing cost and avoiding problems of sterilization and battery change. Surgical port 102 can have a proximal end 110 configured for location on the outside of the patient's body and a distal end 112 sized and configured to extend into the internal portion of the patient's body. Proximal end 110 can include a base 114 and a cannula 116 or tubular body extending from the base towards distal end 112. Surgical port 102 can include channel 118 extending between an opening 120 at proximal end 110 on base 114 and an opening (not shown) at distal end 112. Channel 118 can extend through base 114 and cannula 116 to provide access to an internal portion of the patient's body such that surgical tool 106 (e.g. a laparoscope or an endoscope), can be inserted into the patient's body via channel 118.

Exemplary embodiments of surgical tool tracking system 100 can include a camera 104 mounted to proximal end 110 of surgical port 102. Camera 104 can capture visible spectrum and/or infra-red light or include any other imaging modality suitable for use with surgical procedures. Camera 104 can be configured to capture and store video and/or still images. Camera 104 may also be configured to capture and store audio data. Camera 104 can be configured to capture image data associated with tracking element 108 including still and/or video images of the tracking element 108. Camera 104 may be further configured to capture image data associated with a surgeon performing the medical procedure. For example, camera 104 can capture image data providing surgeon-identifying information such as a surgeon-specific tracking element or marker. An example surgeon-specific marker can include a particular colored glove worn during the medical procedure. The image data associated with the surgeon can also include motion information with respect to surgical tool 106 and/or the surgeon's hand. The motion information can be used to track the motion/path of the surgeon's hands and/or surgical tool 106 during the medical procedure.

In certain exemplary embodiments, camera 104 can be coupled to surgical port 102 via mounting to base 114 of proximal end 110. In other exemplary embodiments, camera 104 can be incorporated with or otherwise integral to base 114. The location of camera 104 with respect to the surgical port 102 can be fixed. That is, camera 104 can be mounted to or otherwise incorporated into the base 114 at a fixed and set position. In other embodiments, the location of camera 104 can be changed or adjusted with respect to surgical port 102. For example, camera 104 can be mounted to base 114 using an adaptor that controls the position and orientation of camera 104.

In certain embodiments, camera 104 can be mounted to the base 114 such that the optical lens/field of view of camera 104 is directed away from the body of the patient. For example, camera 104 can be mounted to the base 114 such that the optical lens/field of view of camera 104 is provided in a direction of tracking element 108 and/or the surgeon's hand as surgical tool 106 approaches and/or is inserted into surgical port 102. In a further example, camera 104 can be mounted to base 114 such that the optical lens/field of view of camera 104 is both directed away from the body of the patient and in a direction of tracking element 108 and/or the surgeon's hand as surgical tool 106 approaches and/or is inserted into surgical port 102. For example, it is contemplated that the optical lens/field of view of camera 104 can be configured to capture image data of tracking element 108 and/or surgeon's hand as surgical tool 106 approaches and is located within surgical port 102.

In particular embodiments, camera 104 can include a light element for illuminating tracking element 108 and/or the surgeon. For example, light element can include an ultra-violet LED that illuminates a UV sensitive feature on tracking element 108. The use of a non-visible light range should not disturb a surgeon preferring to operate in low light conditions. Use of the a UV sensitive feature on tracking element 108 can also have positive effects on the recognition process because tracking element 108 will appear to the system a bright and colorful item in the image, thus making it more distinguishable from the background and/or image noise.

In certain embodiments, camera 104 may be capable of operating on a wired or wireless communication network. Camera 104 may be configured to communicate with other devices using the communication network, the other devices including computers, personal data assistants (PDAs), mobile telephones, and mobile computers. For example, tracking system 100 can include a computer system (not shown). Camera 104 can be in communication with computer system 122 to transmit image data to computer system 122 for analysis and/or storage. Tracking system 100 may include other components capable of acquiring, storing, and/or processing any form or type of data. Any such component may be coupled to or integrated into base 114 or may be communicatively coupled to tracking system 100 and/or computer system 122.

In certain embodiments, tracking system 100 may also include non-optical tracking systems. For example, tracking system 100 can include a transceiver/sensor for detecting and/or tracking an RF (radio frequency) tag associated with surgical tool 106 and/or surgeon. Tracking system 100 can also include an electro-magnetic field sensor for detecting and/or tracking an electromagnetic field associated with or transmitted by surgical tool 106. Other forms and configurations of non-optical tracking methods are considered. The information received using these systems can be used to determine a location of surgical tool 106 and/or the surgeon. Similarly, the received information can be used to track the location/path of motion of surgical tool 106 and/or the surgeon. As outlined below, the location/motion information may be used to determine a surgical step associated with the medical procedure.

Particular embodiments of tracking system 100 can include surgical tool 106. Other embodiments of tracking system 100 may not include surgical tool 106, and may comprise tracking element 108 configured to couple to standard sizes of surgical tools. Surgical tool 106 can be sized and configured to access the internal portion of the patient's body via the surgical port 102. Exemplary embodiments of surgical tools 106 can include laparoscopic instruments (scissors, hooks, knifes, clamps, forceps, coagulating and dissecting electrodes, aspiration needles, retractors, suturing devices, etc.), endoscopes, aspiration lumen, or any other tool or instrument used in conjunction with an access port for conducting a minimally invasive surgical procedure.

Exemplary embodiments of system 100 can include tracking element 108. In certain embodiments, tracking element 108 can be active and/or passive. Exemplary active and passive tracking elements 108 include optical patterns/features readable by the camera 104, RFID tags, LEDs, or any other tag or sensor known in the art. Tracking element 108 can be located at a fixed position with respect the surgical tool 106. For example, tracking element 108 can be located and positioned such that the spatial relationship between tracking element 108 and the handle and/or the tip of surgical tool 106 is known. In one example of tracking system 100, tracking element 108 is removably coupled to the surgical tool 106. In another example, the tracking element 108 can be permanently fixed to the surgical tool 106.

In certain exemplary embodiments, tracking element 108 can include passive markers, such as an optical pattern/feature (color, shape, pattern, bar code, and/or character, etc.) that is readable by camera 104. In an example system, an image of the optical pattern/feature can be processed by an image recognition computer program on the computer system. Image data associated with tracking element 108 can be used to determine the identity of surgical tool 106. For example, tracking element 108 can include a particular feature or combination of features representative of a particular surgical tool 106 or type of surgical tool 106.

As illustrated in FIGS. 1 and 2, an example tracking element 108 can include a disk-shape device. In a particular example, tracking element 108 includes an approximately 4 cm diameter disk coupled proximate the handle portion of the surgical tool 106. The disk can include different and/or alternating colored regions in an angular pattern around the circumference of the disk. The demarcation between the colored regions can be highlighted using a colored line/contour. Similarly, the edge defined by the perimeter of the tracking element can also be highlighted using a colored line/contour. The use of alternating colored regions and/or lines of demarcation can be used by tracking system 100 to help identify patterns/features associated with a particular tracking element 108. It is contemplated that features included on tracking element 108 will vary between surgical tools 106 such that each tool and/or type of tool is separately and individually identifiable.

Image data associated with tracking element 108 can also be used to determine the orientation of surgical tool 106. The image data associated with tracking element 108 can also be used to determine the position of surgical tool 106. The orientation and/or position of surgical tool 106 can be determined with respect to surgical port 102. For example, the position and/or orientation of surgical tool 106 can be compared to a known position and/or orientation of surgical port 102 to determine the relative position/orientation of surgical tool 106. In another example, the orientation and/or position of surgical tool 106 can be determined with respect to the procedure room. For example, position and/or orientation of surgical tool 106 can be compared to a known position and/or orientation of surgical port 102 within the procedure room to determine the "global" position/orientation of surgical tool 106.

Figure 3:
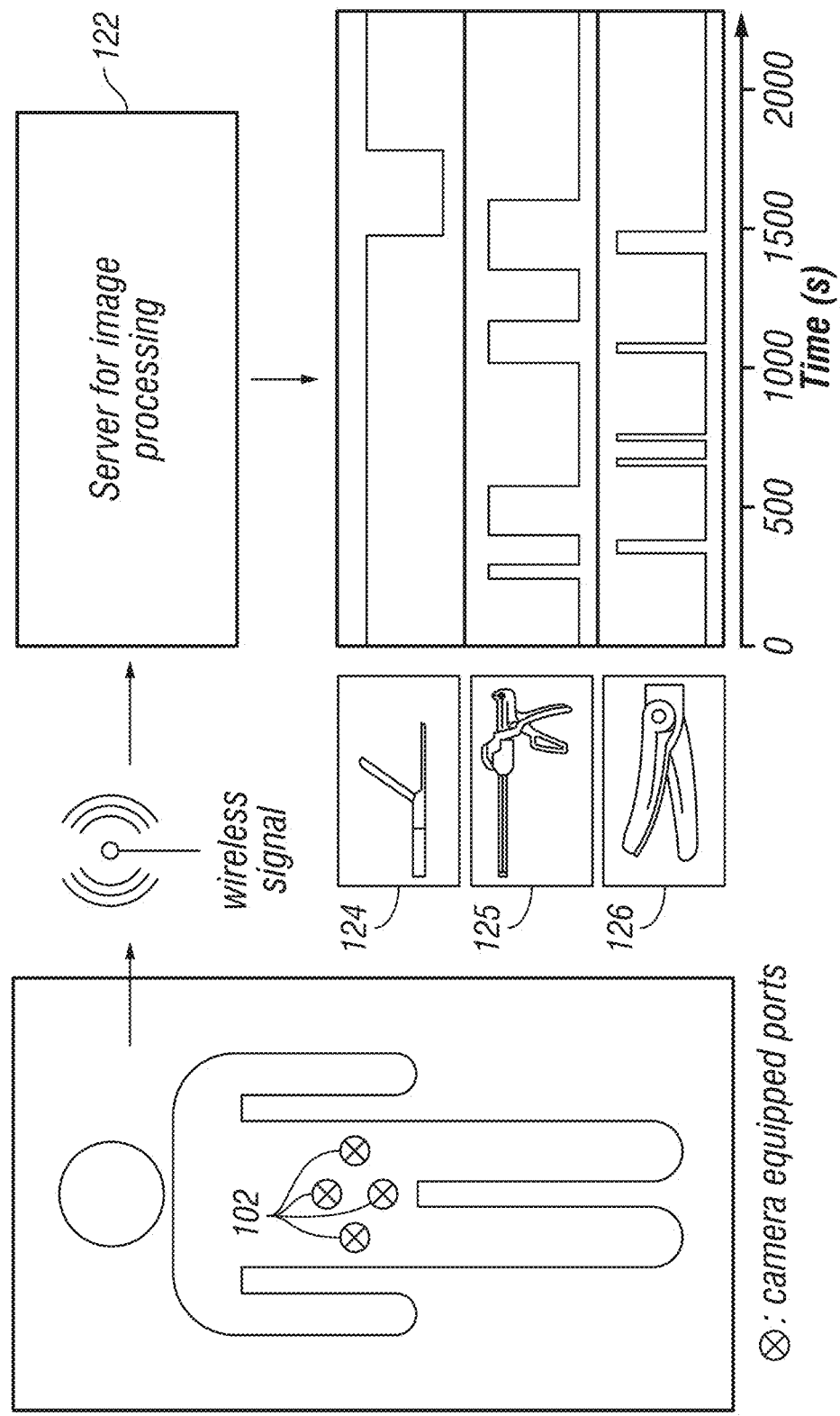
FIG. 3 is a schematic flow diagram of an example tracking system.

FIG. 3 provides a schematic flow diagram of an exemplary embodiment of tracking system 100. In operation, the surgeon can create an access in the body of the patient and surgical port 102 can be inserted into the access. As illustrated in FIG. 3, it is contemplated that multiple accesses and a corresponding number of surgical ports 102 can be used during a particular medical procedure. A surgical tool 106 can be provided to at least one of the surgical ports 102. Image data can be captured by a camera 104 at each of the surgical ports 102 and provided to the computer system 122. The image data can be captured as surgical tool 106 approaches surgical port 102. Likewise, image data can also be captured as surgical tool 106 is inserted into a portion of channel 118 of surgical port 102. The image data can include an image of tracking element 108 and or an image of a portion of the surgeon performing the medical procedure. In an example system, the image data can be associated with data identifying surgical tool 106 (i.e., image data of an identifying feature of tracking element 108) and/or surgeon-specific identification image data.

In certain embodiments, the captured image data can be provided to the computer system 122 for storage and analysis. For example, the image data can be analyzed at an image processing algorithm resident on computer system 122. Computer system 122 can determine tool-specific tracking information. The system can also determine surgeon-specific tracking information. The tracking information can include, for example, the identity of surgical tool 106, the orientation of surgical tool 106, the position of surgical tool 106, the identity of the surgeon, the location and/or motion of the surgeon's hand while manipulating surgical tool 106.

Figure 4:
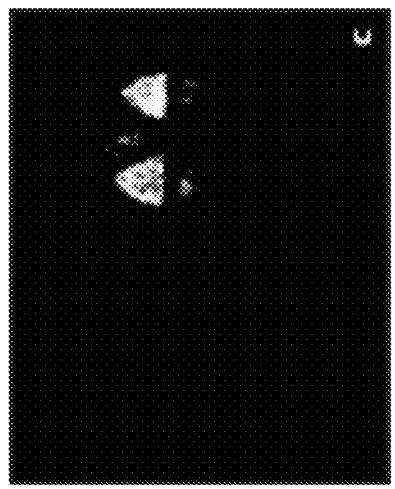
FIG. 4 includes images of example tracking elements.
Figure 4:
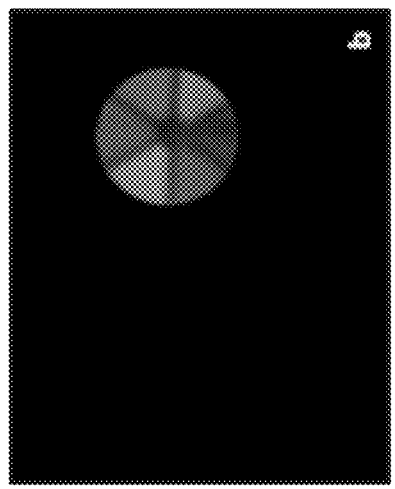
Figure 4:

FIG. 4 provides images of an exemplary embodiment of tracking element 108 captured by camera 104 and analyzed by the image processing algorithm. The image processing algorithm can analyze an image of tracking element 108 extracted from the image data captured by camera 102. The image processing algorithm can recognize color features of tracking element 108 and return an ID associated with surgical tool 106 corresponding to the identified color features. The image processing algorithm can pre-process the image data to reduce the noise of the image and improve its brightness and contrast. Each pixel of the image can be processed to determine if it belongs to a feature of interest. As illustrated in FIG. 4C, a binary image can be produced in which the white pixels have been classified as possible marker pixels. In an example algorithm, each feature (e.g., color) of tracking element 108 is identified in a particular order. When a color is found, the related "flag" is set to (1) (with a (0) flag representative of no color present), with the final output being a binary string composed of (0) and (1). The binary number can be converted in a decimal number which is in turn used to identify surgical tool 106. For example, tracking element 108 illustrated in FIG. 4 can have a binary number of 01001 equating to pink (0), yellow (1), green (0), blue (0), and brown (1). The resulting decimal number (9) is the ID of surgical tool 106.

In particular embodiments, the colors of interest are defined in the HSV space and stored in the image processing algorithm. In this space three indexes define a color according to its hue (H), saturation (S) and brightness (V=value). Colors with too low a value are close to black and can be classified as shadows and ignored. A tracking element 108 color is defined as a three-dimensional matrix in the HSV space and a pixel is assigned to a specific color if its coordinates belong to a valid sector of this space. The values delimitating the matrixes can be defined in advance using sample images of monochromatic markers, acquired from close distance and in good illumination conditions. In an example algorithm, tracking element 108 is detected and isolated from the rest of the image before starting the color classification. For example, as illustrated in FIG. 4, tracking element 108 in the image can be detected using the Circular Hough Transform, a function already implemented and available on MATLAB® Central. This function detects a circle in the image at a given range of radius. The dimension of the radius of tracking element 108 can be set according to the distance of the marker from camera 104. Pixels outside the circle are set to (0). Because the circle should be entirely included in the image to be correctly segmented, it may not be possible to identify the tool when it is inserted too deeply. Therefore, the distance from the tracking element 108 to the camera 104 should be set accordingly. In one example, a minimum distance of 15 cm can be maintained between the camera 104 and the tracking element 108.

In exemplary embodiments, the algorithm will be able to recognize when a misclassification of color occurs and the data can be excluded from the collection. For example, if the algorithm returns a number for a marker which is not used in an operation being performed, or if the system detects none or more than three colors, the data can be excluded from the collection.

Exemplary embodiments can also be configured to prevent a misclassification due to the normal use of a surgical tool 106, e.g., use for many seconds or a few minutes in a row, passing through the same surgical port 102. For example, surgical port 102 and/or the algorithm can be required to evaluate tracking element 108 multiple times. If it happens to have a single different detection in a series of all identical classifications, this is probably a mistake because it is improbable that the surgeon could change the surgical tool 106 so suddenly and use it only for a few seconds. Thus, an example image processing algorithm can be configured to ignore these singularities and consider only the correct classifications.

In exemplary embodiments, the processing algorithm can also provide for a preliminary registration of the marker colors. Because the range in the HSV space is sensitive to change of illumination, it can be helpful to train the image processing algorithm in real operative situations. For example, before starting a medical procedure, the staff can use camera 104 to register images of the monochromatic markers of tracking element 108 in the real illumination condition of the room. The image processing algorithm can use these images to define the range to use for the color search for the following intervention. The calibration can be completed if the operative conditions are consistent.

Tracking system 100 or components thereof may be used in coordination with an information management system resident on the computer system 122 for managing medical procedure information. For example, based on information received from tracking system 100, those individuals responsible for the medical procedure (e.g., a surgeon, anesthesiologist, hospital staff, administration, etc.) can control/manage and evaluate the actual procedure as it happens or post-procedure. The management system can receive image data from the camera 104. The image data can be representative of tracking element 108 associated with a surgical tool 106 being used. The image data need not be associated with a finite set of known tools; instead, the image data can be associated with any tools known in the art to be used during a medical procedure. As outlined above, the image data can also include image data associated with a surgeon.

The identity and location of surgical tool 106 can be determined based on the image data. When determining the identity of surgical tool 106, image data associated with tracking element 108 may be compared with stored data to identify a corresponding stored surgical tool identity. For example, the image data associated with a particular pattern/feature (color, shape, pattern, bar code, and/or character, etc.) can be compared with stored feature data to determine the identity of surgical tool 106 corresponding to the stored image/feature data.

When determining the location of surgical tool 106, image data associated with tracking element 108 (or surgeon) may be compared with location information associated with surgical port 102. For example, using the known location of surgical port 102 with respect to the patient, the location of surgical tool 106 with respect to the patient can be derived. As a result, the location of surgical tool 106 can be determined with respect to the patient, i.e., patient-oriented coordinate system. Using known data regarding the location of the patient within the treatment, the location of surgical tool 106 in the operating room can also be extrapolated, i.e., operating room-oriented coordinate system.

The location of surgical tool 106 can also be determined with respect to surgical port 102. For example, image data associated with the tracking element 108 (or surgeon) may be analyzed to determine the orientation of surgical tool 106 with respect to surgical port 102. For instance, using known size and configuration information of tracking element 108, the image data may be analyzed to determine the distance, angle, rotation, etc., between the surgical tool 106 and the surgical port 102. For example, the distance between the handle of the surgical tool 106 and the opening 120 on the surgical port 102 may be determined. Likewise, the angle and/or rotation between surgical tool 106 and surgical port 102 may be determined.

Similar to the use of tracking element 108 image data, image data associated with the surgeon captured at camera 104 may also be used to determine and identity and location of the surgeon's hand as he manipulates surgical tool 106. For example, image data of a surgeon-specific tracking element or marker may be compared with stored data to determine the identity of the surgeon. In another example, image data of a surgeon-specific tracking element or marker may be compared with location information associated with surgical port 102 to determine the location of the surgeon with respect to the patient and/or the operating room. In another example, image data of the surgeon-specific tracking element or marker may be analyzed to determine the orientation of surgical tool 106 being manipulated by the surgeon with respect to surgical port 102.

The information management system may use the image data to determine the surgical step of the medical procedure being completed. For example, based on the identified surgical tool(s) 106 and/or the time-series of the identified surgical tool(s) 106, a particular step in a given medical procedure may be determined. By comparing the identified surgical tool(s) 106 (or the time-series of identified surgical(s) tools 106) with a known series of steps for a given medical procedure, the system can identify what step the surgeon is in the medical procedure. In another example, the system may also compare the location and/or orientation of surgical tool 106 with a known tool location/orientation to identify the step in the medical procedure. Based on the determined surgical step, the next step in the medical procedure can be anticipated. For example, the surgeon/staff may be provided information regarding the next step such as a checklist or warning. Similarly, the surgeon/staff may be appraised of a pending tool or consumable item need (e.g., sponges, sutures, etc.).

The information management system may also determine procedure management information. Procedure management information may be determined based on the image data associated with the identified surgical step. For example, based on the identified surgical step the system may calculate the time to completion of the medical procedure. This data may be used by the surgical staff anticipate the next step in the surgical procedure and to identify the need for consumable items (sponges, sutures, etc.). This data may also be used by the anesthesiologist to estimate the amount of anesthesia needed to complete the procedure. The calculated time to completion may also take into account time data associated with the current medical procedure. For example, the time data associated with the current medical procedure may indicate that the surgeon is taking ten percent longer to complete the surgical steps than the model procedure. Using this information, the system may estimate that the surgeon will also complete all future steps in the procedure ten percent longer than the model. The system may also take into account historical data associated with a particular surgeon to generate a surgeon-specific model to compare the current procedure.

Figure 5:
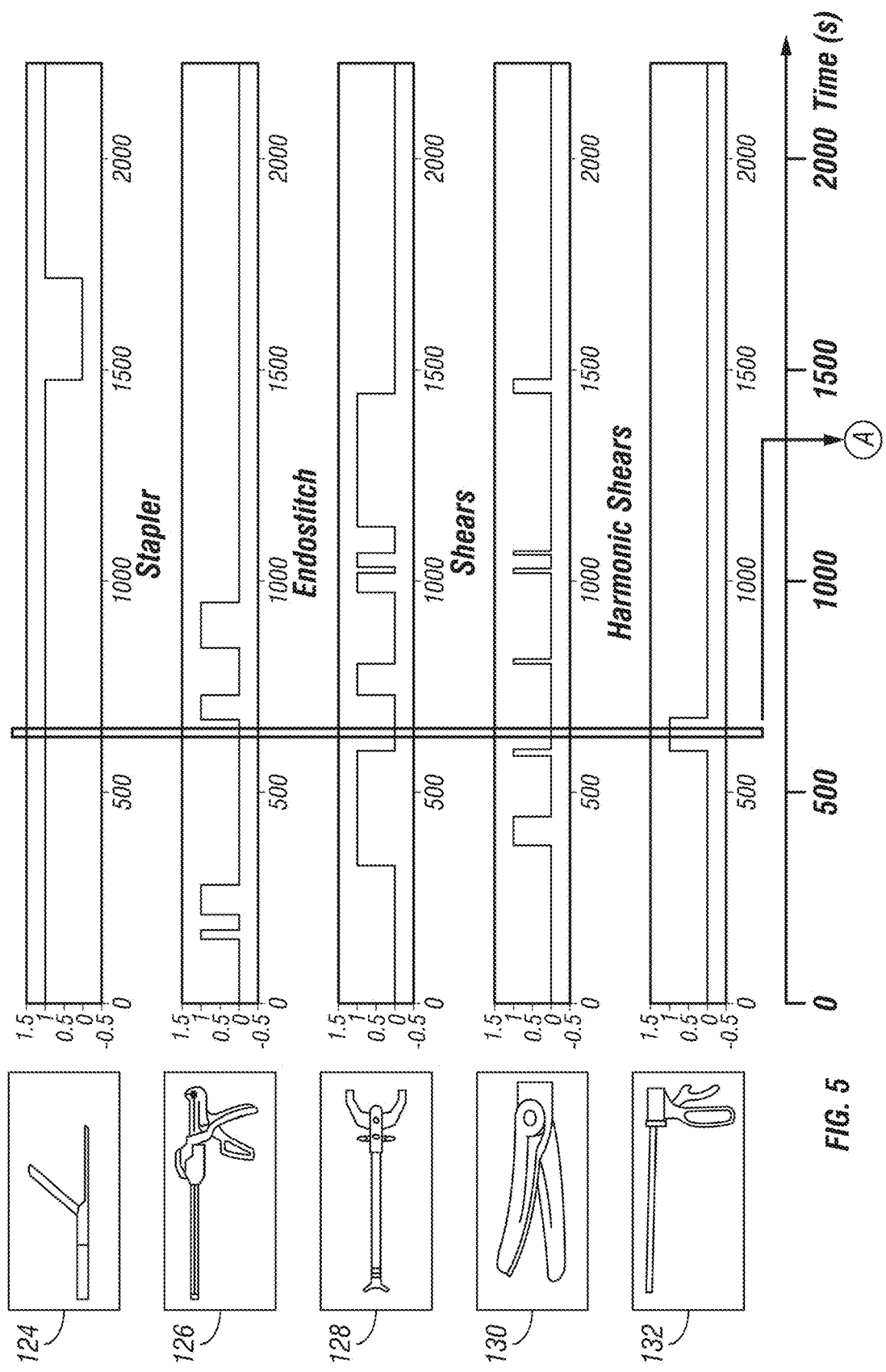
FIG. 5 is a schematic flow diagram of an example tracked medical procedure.
Figure 5:
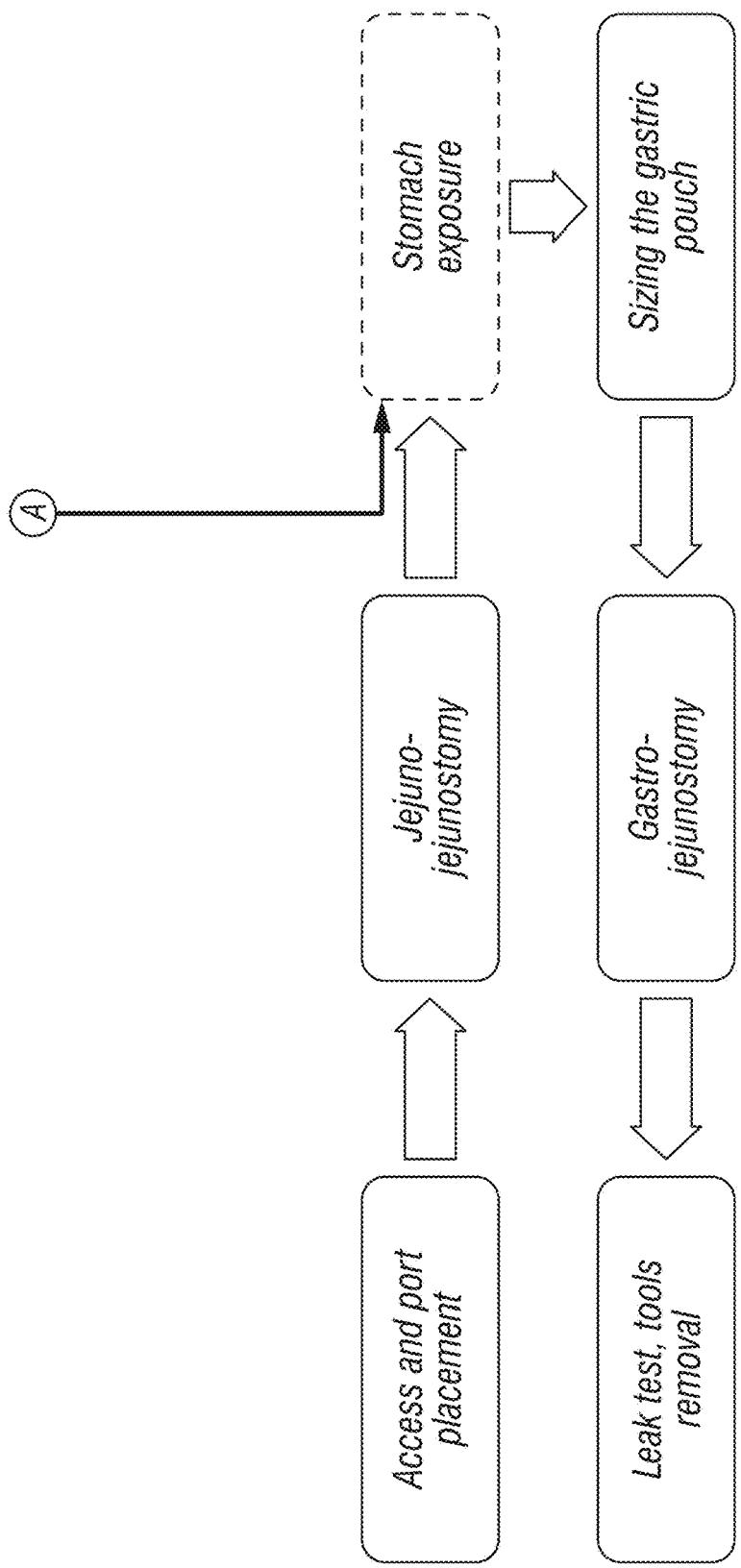

The time of use of surgical tool 106 and/or surgical port 102 may also be determined. For example, the management system may track a time series of the use of the various surgical tools 106 during the medical procedure. Similarly, the length of use of each of surgical tools 106 may also be identified. The number of instrument exchanges (i.e., how many times a particular surgical tool 106 was used, instances where different surgical tools 106 used during the procedure, etc.) may also be identified. As illustrated in FIG. 3, as computer system 122 processes the image data received from the surgical ports 102, the system identifies the surgical port 102 and the particular surgical tool 106 being used and registers a time-series for each of the identified surgical tools 106/surgical ports 102. For example, a first tool 124 shows an initial use at 1500 seconds for approximately 500 seconds. Likewise, a second tool 126 shows an initial use at approximately 300 seconds and intermittent user thereafter. A third tool 128 shows an initial use at approximately 400 seconds and intermittent use thereafter. FIG. 5 provides a time-series for an example surgical procedure. As indicated in FIG. 5, the "Stomach Exposure" step occurs at approximated 600 seconds at which time first tool 124 and a fifth tool 132 are in use and second tool 126, third tool 128, and a fourth tool 130 are not in use.

In certain embodiments, the efficiency of the surgical procedure may be calculated. For instance, the measure of efficiency can compare the current procedure with a model procedure. For example, to calculate the efficiency of the surgical procedure, the amount of time it takes the surgeon to complete the current procedure may be compared with a time of the model procedure. Based on this comparison, an efficiency of the procedure and/or particular steps within the procedure may be determined based on how closely the actual times compare to the model time.

In particular embodiments, a skill level associated with a surgeon performing the surgical procedure may also be calculated. The skill level of the surgeon may take into account the surgeon's efficiency at a particular procedure. In calculating skill level, image data may be used to track the smooth motion of surgical tool 106 during the procedure. For example, using image data associated with tracking element 108 and/or the surgeon's hand, the fluency of motion of surgical tool 106 and/or the surgeon's hand may be tracked and compared to a model for surgical tool 106 movement. The skill level may also include a consumable use estimate. For example, the use of particular consumable items including, for example, sponges, sutures, etc., may be tracked and compared to a model consumption range for the identified procedure. Using image data, use of consumables exceeding (or less than) the model range can be identified and an appropriate impact on the skill level applied.

It is contemplated that more than one surgical tool 106 can be used (sequentially) at a single surgical port 102. It is also contemplated that the disclosed tracking system 100 and information management system can utilize multiple surgical ports 102 (sequentially or simultaneously) each using multiple surgical tools 106. The image data can include image data from each of surgical ports 102 representative of each of surgical tools 106. When more than one surgical port 102 is used, image data received from the second camera 104 associated with the second surgical port 102 is representative of the tracking element 108 associated with the second surgical tool 106. As outlined above, the identity of a second surgical tool 106 can be determined based on the captured image data.

Using this image data, the corresponding surgical step can be determined. When determining procedure management information, image data associated with the newly determined surgical step can be compared with the medical procedure. The previously determined surgical step may also be considered and compared with the newly determined surgical step. Using this information, irregularities in the medical procedure can be identified and warnings provided to the surgeon/staff. For example, the surgeon may have completed step 1 of the medical procedure and the next identified step is step 3, i.e., the surgeon skipped step 2. A warning may be provide to the surgeon/staff indicating that a step in the medical procedure was missed.

It should be appreciated that the logical operations described herein with respect to the various figures may be implemented (1) as a sequence of computer-implemented acts or program modules (i.e., software) running on a computing device (e.g., the computer system), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 6:
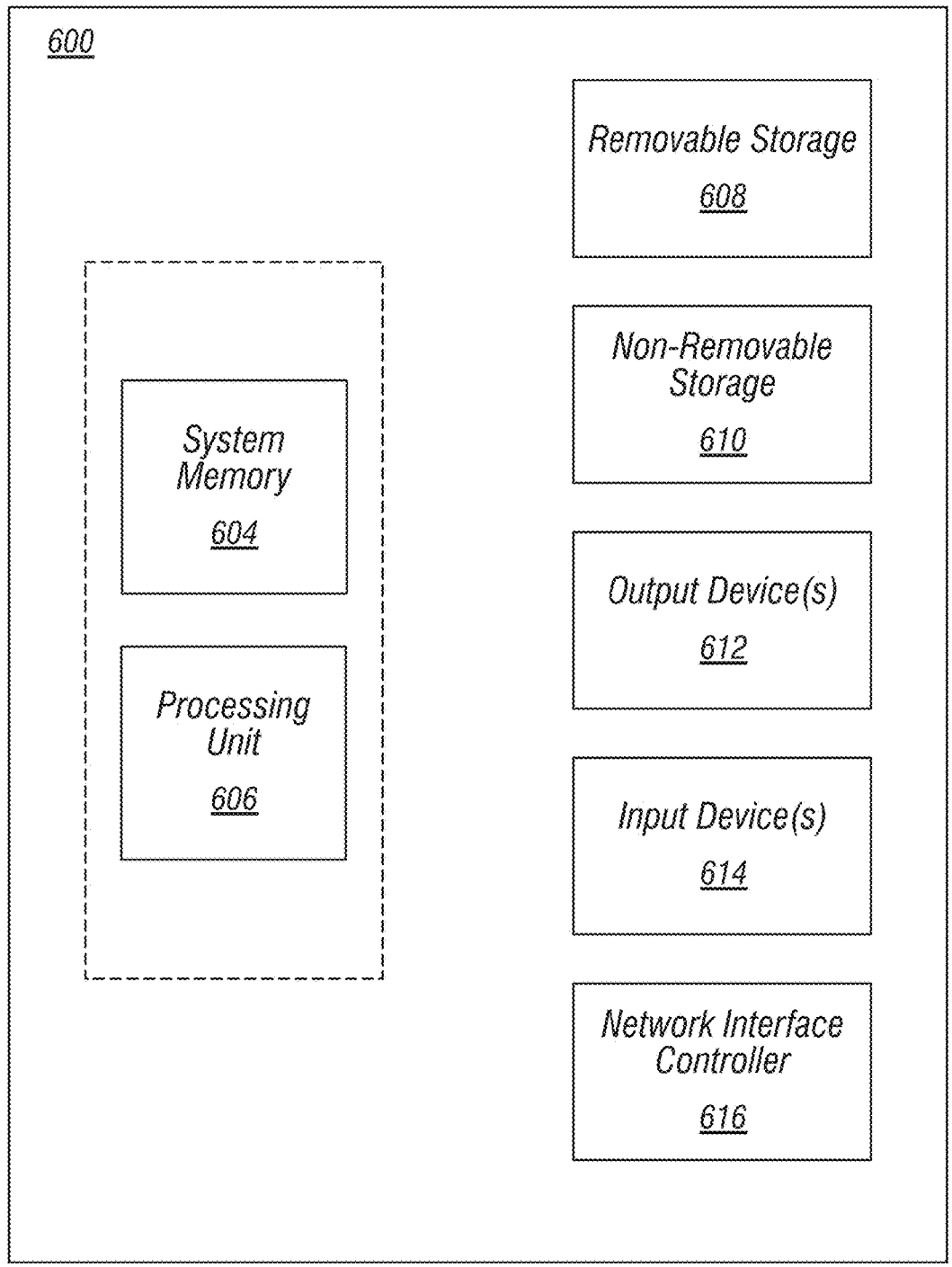
FIG. 6 is a schematic computer system architecture of an exemplary system.

When the logical operations described herein are implemented in software, the process may execute on any suitable computing architecture or platform. For example, the functions of the PCB, processor, control circuitry, and vehicle electronics control unit, as described above, may be implemented on any suitable computing architecture or platform. An exemplary implementation illustrated in FIG. 6 provides one example of a computing device upon which embodiments of the invention may be implemented. A computing device 600 may include a bus or other communication mechanism for communicating information among various components of computing device 600. In one basic configuration, computing device 600 typically includes at least one processing unit 606 and system memory 604. Depending on the configuration and type of computing device, system memory 604 may be volatile (such as random access memory (RAM)), non-volatile (such as read-only memory (ROM), flash memory, etc.), or some combination of the two. One such configuration is illustrated in FIG. 6 by dashed line 602. A processing unit 606 may be a standard programmable processor that performs arithmetic and logic operations necessary for operation of computing device 600.

Computing device 600 may have additional features and functionality. For example, computing device 600 may include additional storage such as removable storage 608 and non-removable storage 610 including, but not limited to, magnetic or optical disks or tapes. A computing device 1300 may also contain network connection(s) 616 that allow the device to communicate with other devices. Computing device 600 may also have input device(s) 614 such as a keyboard, mouse, touch screen, etc. Output device(s) 612 such as a display, speakers, printer, etc. may also be included. The additional devices may be coupled to the bus in order to facilitate communication of data among the components of computing device 600.

In exemplary embodiments, processing unit 606 may be configured to execute program code encoded in tangible, computer-readable media. Computer-readable media refers to any media that is capable of providing data that causes the computing device 600 (i.e., a machine) to operate in a particular fashion. Various computer-readable media may be utilized to provide instructions to processing unit 606 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 606 may execute program code stored in the system memory 604. For example, the bus may carry data to system memory 604, from which processing unit 606 receives and executes instructions. The data received by system memory 604 may optionally be stored on a removable storage 708 or the non-removable storage 610 before or after execution by the processing unit 706.

In exemplary embodiments, computing device 600 can include a variety of computer-readable media. Computer-readable media can be any available media that can be accessed by device 600 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 604 and removable storage 608 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 600. Any such computer storage media may be part of computing device 600.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device can include a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Experimental Results

The identification algorithm and improvement in the markers resulted in higher recognition rates for the system. In an initial version, the markers were simple disks of cardboard and have been printed using an inkjet printer. The final result was indeed rough, with imperfect homogeneous colors that could lead the identification system to mistakes. Furthermore, this kind of printer does not allow a good control on the final result, so that the real marker colors appeared different from what has been designed on the computer. This was a problem because it produced colors which were too dark and too close in the HSV space. On the computer, it was planned to have colors with distant hues and good saturation and brightness. Light and brilliant colors reduce the risk of misclassification in presence of shadows. In the second version, with the addition of the circle detection, a black circle has been added around the marker to make it more distinguishable from the background.

Figure 7:
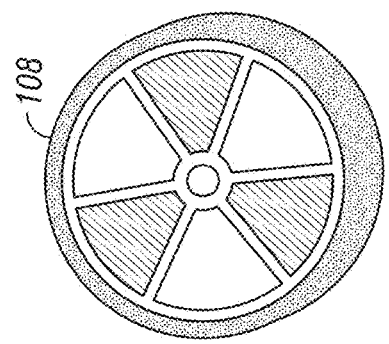
FIG. 7 is a plan view of example tracking elements.
Figure 7:
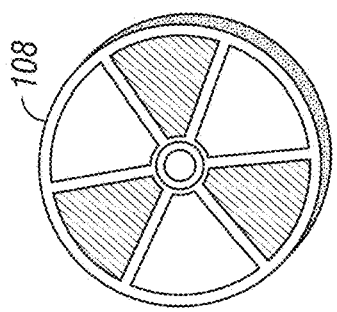
Figure 7:
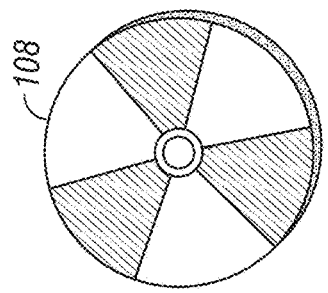

In the final version, the markers were printed on lucid paper by professional typography. The paper was glued to disks of black foam board. This product presented the helpful characteristics of accuracy, brightness and homogeneity, and brought a consistent improvement in the percentage of correct classifications. In FIG. 7, samples of the different versions are visible. Table 1 illustrates the corresponding range in the HSV space for each color: they had to be redefined for the different marker prototypes.

TABLE 1

Range in the HSV Space for Each Color According to Marker Version

|  |  | Pink | Yellow | Green | Blue | Brown-orange | Red |
|---|---|---|---|---|---|---|---|
| First marker type | H | 0.8-0.03 | 0.125-0.2 | 0.3-0.54 | 0.55-0.65 | 0-0.07 | — |
|  | S | 0.15-0.65 | 0.35-0.8 | 0.46-1 | 0.55-1 | 0.65-1 | — |
|  | V | 0.6-1 | 0.73-1 | 0.15-0.6 | 0.35-0.85 | 0.3-0.85 | — |
| Second marker type | H | 0.8-0.02 | 0.125-0.2 | 0.29-0.54 | 0.56-0.65 | 0.03-0.05 | — |
|  | S | 0.45-0.85 | 0.35-0.8 | 0.3-0.8 | 0.5-1 | 0.5-1 | — |
|  | V | 0.5-1 | 0.73-1 | 0.15-0.7 | 0.2-0.85 | 0.4-1 | — |
| Third marker type | H | 0.8-0.95 | 0.1-0.2 | 0.25-0.32 | 0.49-0.6 | — | 0-0.07 |
|  | S | 0.4-0.8 | 05.-0.9 | 0.5-0.9 | 0.6-1 | — | 0.6-1 |
|  | V | 0.55-0.84 | 0.55-0.84 | 0.72-1 | 0.72-1 | — | 0.5-0.8 |

As demonstrated in Table 1, the more uniform markers of the third implementation allowed to narrow the ranges and to increase the distance between colors in the HSV space, thus reducing the possibility of misclassification. This also permitted the replacement of brown with red, a lighter color, less influenced by the presence of shadows.

For the first implementation 25 markers (first kind) were evaluated in a set of 153 pictures, at 3 distances from the camera (5, 20 and 30 cm) showing the laparoscopic tool at 2 different orientations (up or down). In 82 of these images the classifications were correct (53.6%). Misclassifications were due to missed recognition of the marker or to classification of other objects as marker. The number of total false positive was 49, while the number of false negative was 46. Table 2 and Table 3 illustrate how each color contributes to the misclassification. It is immediately visible that green was the most problematic color: it was recognized in only 30 of the 63 pictures where it was present. Furthermore, often the shadows present on the blue surgical glow used in this test are classified as green and cause false positive. Clearly the definition in the HSV field of the green color was incorrect.

TABLE 2

Number of False Negative Recognitions per Color in the First Version of the System
FALSE NEGATIVE

| PINK | 8 |
| YELLOW | 0 |
| GREEN | 33 |
| BLUE | 1 |
| BROWN | 4 |

TABLE 3

Number of False Positive Recognitions per Color in the First Version of the System
FALSE POSITIVE

| PINK | 0 |
| YELLOW | 3 |
| GREEN | 18 |
| BLUE | 16 |
| BROWN | 12 |

Beside the particular case of green, the number of false negative is not very high, which indicates the algorithm is often able to recognize a color when it is present. More problematic is the situation regarding the false positive, 94% of this kind of misclassification were caused by colors with a low value. This can happen because some shadows present on the glow or on the skin can belong to those ranges of HSV indexes. Colors with such low values have been avoided in the final version of the markers, when it was possible to optimize the printer outcome. Only a few markers have been correctly classified in the whole set of pictures: blue-brown, yellow-blue and pink-yellow-blue. Two markers were always misclassified: green-pink and yellow-green-pink (there is clearly a correlation with the green setting problem).

Another observation concerns the marker composition: whether monochromatic markers more visible than the others, or vice-versa. The analysis of the available data suggests that this factor does not have a very significant influence, as shown in Table 4 (incorrect classifications are shown on top at each bar graph, with correct classifications shown at the bottom of each bar graph).

TABLE 4

Number and Percentage of Correct Classifications, Depending on Marker Kind
CLASSIFICATION PER MARKER TYPE

| MARKER TYPE | CORRECT CLASSIFICATION | INCORRECT CLASSIFICATION |
|---|---|---|
| 1 COLOR | 14 (47%) | 16 (53%) |
| 2 COLORS | 39 (65%) | 21 (35%) |
| 3 COLORS | 29 (46%) | 34 (54%) |

There is a slight prevalence of correct classification for the markers with two colors, but the cause is hard to determine. It is possible that some difficulties occurred using the three-color marker: even if at least half of the disk is always visible, sometimes one sector is partially outside of the image or more in shadow compared to the other two, a problem which has no influence with only two colors. One important aspect that is possible to affirm now is that it is not necessary to have a wider colored area to make a marker recognizable. The sectors currently used bring results comparable with monochromatic markers.

Also the distance or the position from the camera does not have a particular influence on the result. The 82 correct classifications are almost evenly distributed along the six position tested in this trial. It could happen that the marker may appear blurry in the image when it was not on the line of focus of the camera (contours are clear only for low position, 30 or 20 cm far). Nevertheless, its identification is not compromised. This gives a good margin for future changes in the camera orientation.

The set of images tested for the second implementation was wider: 24 markers were tried, in eight different positions (at 15, 19, 20 or 25 cm from the camera, up or down), for a total of 192 images. In the set of 192 images, 155 had been classified correctly (80.7%). The causes of mistake were wrong detection of the circle in the image (11 cases, occurrence of 5.7%) or misclassification of the colors present in the image (26 cases, 13.6%), with 11 false positive and 17 false negative. The percentages of correct classification in different positions are uniformly distributed, showing that there is not evidence of an influence of the tool position on the marker identification.

The influence of the color on the misclassification is visible in Table 5 and Table 6.

TABLE 5

Number of False Positive Recognitions per Color in the Second Version of the System
FALSE POSITIVE

| | |
|---|---|
| PINK | 0 |
| YELLOW | 2 |
| GREEN | 4 |
| BLUE | 0 |
| ORANGE | 5 |

TABLE 6

Number of False Negative Recognitions per Color in the Second Version of the System
FALSE NEGATIVE

| | |
|---|---|
| PINK | 4 |
| YELLOW | 2 |
| GREEN | 5 |
| BLUE | 2 |
| ORANGE | 4 |

Green and orange have a slightly stronger influence on this type of mistake. For the false positives, it typically happens that blue is classified as green and pink as orange. It should be possible to reduce this problem by using colors with a higher distance between the value ranges. In any case, there is a sensible improvement from the first implementation, as a result of the background noise reduction.

The last test was performed on the final version of the algorithm, presenting the circle detection but no filtering after the color identification, with a set of 25 markers professionally printed and assembled on foam board disks. The pictures extracted from the video are at 15, 20 and 25 cm from the camera and present 4 different orientation of the pseudo-tool (up, down, left and right), for a total amount of 300 pictures. The significant improvement of the quality of the markers and the small modification of the code produced impressive results: 96.66% of correct classifications. The percentages at each distance are shown in Table 7.

TABLE 7

Percentages of Correct Classification Obtained by the Final Version of the System Distributed along the Different Distances from the Camera
PERCENTAGE OF CORRECT CLASSIFICATIONS

| DISTANCE FROM CAMERA | CORRECT CLASSIFICATION |
|---|---|
| 15 cm | 98 |
| 20 cm | 97 |
| 30 cm | 95 |

Another important result of this last test is that an error did not occur for incorrect detection of the marker contour. The system was consistently able to identify the marker in the picture. This improvement appears to depend on the better quality of the markers, because no modification has been produced on the related part of the algorithm. Knowledge that the detection of the marker is highly dependable will be important when the algorithm is trained to identify its own misclassification. The ten errors were due to confusion between colors closed in the HSV space, such as false presence of pink or yellow when only the red color is present. This happens in rare occasions, only when the light hits the marker in such a way that produces shades of different colors.

The results obtained so far show that the modified trocar could be a valid resource, in the wider project of operating room assessment, to perform instrument recognition. It is contemplated that a surgical tool tracking system can be used with a modified trocar to record a simulation of a laparoscopic cholecystectomy. This operation has several desired characteristics: it is not excessively long, it is performed following a standard sequence of steps, and needs only a main port for the most specific tools (the other accesses are secondary and mainly used for graspers). The video recorded by the trocar during the operation will then be sampled in frames and in each of them the software will try to identify the marker of the tool. A comparison between the real tool sequence and the one identified by the software will show if the system is effective to its purpose.

While the foregoing description and drawings represent examples of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed examples are, therefore, to be considered in all respects as illustrative and not restrictive, the scope of the invention being indicated by the appended claims and not limited to the foregoing description.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention, as defined by the following claims.

REFERENCES

The contents of the following references are incorporated by reference herein:

Agarwal S, Joshi A, Finin T, Yesha Y. A Pervasive Computing System for the Operating Room of the Future. Mobile Networks and Applications. 2007; 12:215-28.

Blum T, Padoy N, Feussner H, Navab N. Modeling and online recognition of surgical phases using Hidden Markov Models. *Med Image Comput Comput Assist Interv.* 2008; 11:627-35.

Doryab A, Bardram J E. Designing activity-aware recommender systems for operating rooms. *Proceedings of the 2011 Workshop on Context-awareness in Retrieval and Recommendation.* New York, N.Y., USA; 2011; 43-6.

Doryab A, Togelius J, Bardram J. Activity-aware recommendation for collaborative work in operating rooms. *Proceedings of the 2012 ACM international conference on Intelligent User Interfaces.* New York, N.Y., USA; 2012; 301-4.

Kranzfelder M, Schneider A, Blahusch G, Schaaf H, Feussner H. Feasibility of opto-electronic surgical instrument identification. Minim Invasive Ther Allied Technol. 2009; 18(5):253-8.

Liu C C, Chang C H, Su M C, Chu H T, Hung S H, Wong J M, et al. RFID-initiated workflow control to facilitate patient safety and utilization efficiency in operation theater. *Comput Methods Programs Biomed.* 2011; 104(3):435-42.

Marjamaa R, Vakkuri A, KirvelÄ O. Operating room management: why, how and by whom? *Acta Anaesthesiologica Scandinavica.* 2008; 52:596-600.

Neumuth D, Loebe F, Herre H, Neumuth T. Modeling surgical processes: a four-level translational approach. *Artif Intell Med. Netherlands.* 2011; 51(3):147-61.

Neumuth T, Jannin P, Schlomberg J, Meixensberger J, Wiedemann P, Burgert O. Analysis of surgical intervention populations using generic surgical process models. *Int J Comput Assist Radiol Surg.* 2011; 6:59-71.

Neumuth T, Jannin P, Strauss G, Meixensberger J, Burgert O. Validation of knowledge acquisition for surgical process models. *J Am Med Inform Assoc.* 2009; 16(1):72-80.

Neumuth T, Strauß G, Meixensberger J, Lemke H, Burgert O. Acquisition of Process Descriptions from Surgical Interventions. *Lecture notes in computer science.* 2006; 4080:602-11.

Padoy N, Blum T, Ahmadi S- A, Feussner H, Berger M-O, Navab N. Statistical modeling and recognition of surgical workflow. *Medical Image Analysis.* 2012; 16:632-41.

Schoepp H. Surgical Navigation System. United States 2012.

What is claimed is:

1. A surgical tool tracking system comprising:
a surgical port comprising an opening at a proximal end configured to be located outside a body of a patient and a distal end configured to be located within an internal portion of the body of the patient, and a channel extending between the proximal end and the distal end;
a tracking element coupled to a surgical tool comprising a handle, wherein:
the surgical tool is configured to perform a surgical step of a medical procedure;
the tracking element comprises a disk of a known diameter proximal to the handle; and
the disk has a configuration comprising alternating colored regions in an angular pattern around the disk;
a camera mounted to the proximal end of the surgical port and configured to capture image data associated with the tracking element, wherein:
the surgical port is a trocar, the trocar comprising a base at the proximal end and a cannula at the distal end, wherein the camera is mounted to the base;
the camera is configured to capture the image data associated with the tracking element as the surgical tool approaches the surgical port and as the surgical tool is located within the surgical port, and wherein the image data comprises:
a location of the surgical tool; and
motion information of the surgical tool; and
a computer system, wherein the camera is in communication with the computer system to transmit the image data to the computer system, wherein:
the camera is directed away from the distal end of the surgical port;
the image data associated with the tracking element is analyzed by the computer system using the known diameter and configuration of the disk in order to:
determine an orientation of the surgical tool with respect to the surgical port;
determine a distance between the handle of the surgical tool and the opening at the proximal end of the surgical port;
use the location and motion information of the surgical tool to identify the surgical step of the medical procedure; and
determine procedure management information based on the image data associated with an identified surgical step, wherein the procedure management information includes a time to completion of the medical procedure.

2. The surgical tool tracking system of claim 1, wherein the camera is in a fixed position with respect to the surgical port.

3. The surgical tool tracking system of claim 1, wherein the time to completion of the medical procedure is compared to a model procedure.

4. The surgical tool tracking system of claim 1, wherein the camera is directed towards the tracking element.

5. The surgical tool tracking system of claim 1, wherein:
the camera comprises an ultraviolet light;
the tracking element comprises an ultraviolet sensitive feature; and
the ultraviolet light is configured to illuminate the ultraviolet sensitive feature.

6. The surgical tool tracking system of claim 1, wherein the camera includes a light element for illuminating the tracking element.

7. The surgical tool tracking system of claim 1, wherein the computer system is configured to analyze the image data to determine a distance and angle between the surgical tool and the surgical port.

8. The surgical tool tracking system of claim 1, wherein the tracking element includes at least one of a color, a shape, a pattern, bar code, and a character.

9. The surgical tool tracking system of claim 1, further comprising a surgical tool, wherein:

the surgical tool is sized and configured to access the internal portion of the body of the patient through the channel of the surgical port; and the tracking element is coupled to the surgical tool.

10. The surgical tool tracking system of claim 1, wherein the tracking element corresponds to at least one of an identity of the surgical tool, an orientation of the surgical tool, and a position of the surgical tool.

11. The surgical tool tracking system of claim 1, wherein the tracking element is positioned a location proximate a handle associated with the surgical tool.

12. The surgical tool tracking system of claim 1, wherein the camera is further configured to capture image data associated with a surgeon.

* * * * *

UNITED STATES PATENT AND TRADEMARK OFFICE
CERTIFICATE OF CORRECTION

PATENT NO. : 10,470,687 B2
APPLICATION NO. : 14/099430
DATED : November 12, 2019
INVENTOR(S) : Garbey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 155 days.

Signed and Sealed this
Twentieth Day of December, 2022

Katherine Kelly Vidal
*Director of the United States Patent and Trademark Office*